United States Patent [19]

Rogers

[11] 4,416,778

[45] Nov. 22, 1983

[54] MEANS FOR PREPARING NEOCYTE ENRICHED BLOOD

[75] Inventor: Charles H. Rogers, Duxbury, Mass.

[73] Assignee: Neocyte, Inc., Rockland, Mass.

[21] Appl. No.: 313,343

[22] Filed: Oct. 20, 1981

[51] Int. Cl.³ .............................................. B01D 21/26
[52] U.S. Cl. .................................. 210/516; 210/927; 206/568; 494/16
[58] Field of Search ................ 210/789, 927, 516, 117, 210/136; 128/214 D; 233/26; 206/568, 570

[56] References Cited

U.S. PATENT DOCUMENTS

| 3,800,947 | 4/1974 | Smith | 210/789 X |
| 3,885,735 | 5/1975 | Westbert | 210/927 X |
| 4,007,871 | 2/1977 | Jones et al. | 210/789 X |
| 4,268,393 | 5/1981 | Persidsky et al. | 210/927 X |
| 4,278,202 | 7/1981 | Westberg | 210/927 X |

Primary Examiner—Thomas G. Wyse
Attorney, Agent, or Firm—Cesari and McKenna

[57] ABSTRACT

A method of preparing neocyte-enriched blood is disclosed wherein a contained sample of whole blood is centrifuged at high speed so as to distribute the blood components in said chamber along a density continuum. Following the high-speed centrifuging step, the blood components in the first chamber are partitioned by transferring those components beyond a selected partition line in the first chamber from the spin axis to a second chamber so that the blood components in the first and second chambers can be used independently. Apparatus for effecting the separation and partitioning of the blood in a completely sterile environment is also disclosed.

18 Claims, 8 Drawing Figures

MEANS FOR PREPARING NEOCYTE ENRICHED BLOOD

This invention relates to a method for preparing neocyte enriched blood. It relates more particularly to a method for segregating neocyte enriched blood from blood gerocytes and to apparatus for accomplishing same.

BACKGROUND OF THE INVENTION

The red blood cells or erythrocytes in donor blood have a certain life span. Actually, human blood contains more or less equal portions of red blood cells of ages between about 0 and 120 days. Thus, in any given sample, there is a certain percentage of younger blood cells or so-called neocytes and a certain percentage of older cells called gerocytes. Also, human blood contains a relatively large amount of iron, on the order of 108 mg/dl of red cells. Furthermore, the iron content is relatively uniform regardless of the average cell age of the blood sample. There are some patients, those suffering from chronic anemias for example, who depend upon repeated blood transfusions for their survival. Indeed, they may receive donor blood at such a rate that their systems are unable to entirely dispose of the iron content of that blood with the result that the patients suffer from iron overload and may die from complications resulting from that cause.

Since the contribution to iron overload is the same from the oldest transfused red cells which survive only a few hours as from the youngest ones which circulate in the body for months, it has been obvious for some time that a blood transfusion for patients such as this would be much more effective in terms of the ratio of physiological benefit to iron overload if the older red cells were removed from the donor blood and only the younger cells administered to the patient.

It has also been recognized that the red cells in donor blood have a certain density distribution. Indeed, it turns out that the older red blood cells are more dense than the younger ones. Using this knowledge, attempts have been made to separate the red cells in a donor sample according to their densities so as to segregate the younger red cells or neocytes from the older cells or gerocytes. Some such attempts, described for example in the following publications (copies of which are attached hereto), involve centrifuging the donor blood:

Murphy, John R., "Influence of temperature and method of centrifugation on the separation of erythrocytes", *J. Lab. Clin. Med.*, August, 1973, pp. 34–341; Corash, Lawrence M., et al, "Separation of erythrocytes according to age on a simplified density gradient", *J. Lab. Clin. Med.*, July, 1974, pp. 147–151; Piomelli, Sergio, et al, "Separation of younger red cells with improved survival in vivo: An approach to chronic transfusion therapy", *Proc. Natl. Acad. Sci. USA* 75 (1978), pp. 3474–3477; and Vettore, Luciano, et al, "A New Density Gradient System for the Separation of Human Red Blood Cells", *American Journal of Hematology*, 8:291 at Volume 8 (1980), pp. 291–297.

The usual technique for separating whole blood in accordance with the density of the blood fractions is to place the blood sample in a container and spin the container about an axis perpendicular to the container axis at a high speed to subject the container contents to a centrifugal force on the order of 2,000 G. The force exerted on the contained blood sample causes the heaviest, most dense blood fractions such as the red cells to accumulate at the bottom or closed end of the container distal from the spin axis, while the less dense fractions, such as the blood plasma, accumulate at zones in the container progressively closer to the spin axis. Typical apparatus for effecting density separation of blood fractions by centrifuging are disclosed in the above mentioned Murphy article, as well as in the following U.S. patents:

| | | | |
|---|---|---|---|
| 3,064,647 | Earl | 3,935,113 | Ayres |
| 3,750,645 | Bennet et al | 3,945,928 | Ayres |
| 3,800,947 | Smith | 4,187,861 | Heffernan |
| 3,887,464 | Ayres | 4,189,385 | Greenspan |

As described in some of these prior references, the Ayres patents for example, the centrifuged container defines upper and lower chambers separated by a check valve. The whole blood is placed in the upper chamber and the container is accelerated up to high speed. Under the high G force, the heavier blood fractions tend to find their way to the bottom of the upper chamber and pass through the check valve into the lower chamber. Such apparatus does effectively separate whole blood into its gross fractions; i.e. the plasma having a density of about 1.01 g/cc is separated from the blood cells having an average density of 1.07 g/cc. This is because that density difference is quite significant at centrifuge speeds. Also, according to Murphy and others, there is apparently also some separation of the red blood cells themselves in accordance with a density gradient.

While Murphy and others have drawn off samples of the centrifuged blood at different zones in a container using quite complicated and time-consuming mixing and aspirating techniques in order to test and verify that some separation of cells according to age has occurred, until now there has been no effective way of readily segregating or partitioning the younger red blood cells from the older ones in a sterile environment so that the younger cells would be available for immediate transfusion to a needy patient.

SUMMARY OF THE INVENTION

Accordingly, the present invention aims to provide an improved method for obtaining neocyte enriched blood.

Another object of the invention is to provide a method for segretating red blood cells or erythrocytes according to their age.

Another object of the invention is to provide a method for partitioning the red blood cells in donor blood at a selected point in a blood cell age or density continuum.

A further object of the invention is to provide a method for segregating old and new blood cells which can be performed quickly and reliably by relatively unskilled personnel.

Still another object of the invention is to provide apparatus for carrying out the above objects.

Another object of the invention is to provide apparatus for segregating or partitioning the red blood cells in donor blood at a selected point in a blood cell age or density continuum.

Another object of the invention is to provide apparatus for preparing neocyte enriched blood in a completely sterile environment.

A further object of the invention is to provide a method and apparatus for separating or distribution and a partitioning blood neocytes and blood gerocytes in a sterile condition so that both of these blood components can be used independently of the other.

Other objects will, in part, be obvious and will, in part, appear hereinafter.

The invention accordingly comprises the several steps and the relation of one or more of steps with respect to each of the others, and the apparatus embodying the features of construction, combination of elements and arrangement of parts which are adapted to effect such steps, all as exemplified in the following detailed description, and the scope of the invention will be indicated in the claims.

In accordance with this method, donor whole blood is introduced into one chamber of a sealed container system comprising first and second chambers connected in series by a valve conduit. The valve is closed initially so that the blood remains in the one chamber. Next, the container system is centrifuged at high speed, e.g. 2,000 G, with the conduit end of the one chamber being distal to the spin axis and the valve remaining closed, thereby preventing flow of fluid between the two chambers during centrifuging. The high-speed centrifuging step is continued until the whole blood in the one chamber separates into blood fractions distributed along a density continuum, the least dense fractions collecting proximal to the spin axis and the most dense fractions accumulating adjacent the conduit distal to the spin axis.

Following this, near the end of the centrifuge cycle only after the container system has slowed to a relatively low speed, e.g. 200 G, the valve is opened. This establishes communication between the two chambers so that the older denser blood cells distal to the spin axis flow through the conduit into the other chamber. The flow is continued until all of the cells from the first chamber below a selected imaginary partition line in the density continuum established during centrifuging have entered the second chamber. In other words, the blood fraction density continuum formed in the one chamber by centrifuging is partitioned at a selected level or slice in that continuum so that only red blood cells located below that level exceeding a selected density flow into the other chamber, the less dense cells remaining in the one chamber. Then the flow is stopped.

The volume of blood cells entering the second chamber can be controlled by regulating fluid flow into the other chamber. For example, it can be controlled by properly selecting the volume of the other chamber. Obviously, as the volume of that chamber is made smaller, fewer cells can flow into that chamber from the one chamber, i.e. the partition line in the blood fraction density continuum formed in the one chamber is lowered, and vice versa. Thus, by appropriately selecting the other chamber volume, one can control the average density of the red blood cells remaining in the one chamber after the separation and partitioning steps.

Since there is a direct relationship between red cell density and age as described above, one can also control the mean age of the cells remaining in the one chamber. For example, one might select the other chamber volume so that it receives half of the red cells originally present in the one chamber. According to the Piomelli article cited above (FIG. 3), the 50% red cells (rabbit blood) remaining in the one chamber will survive in circulation for almost their finite life-span of 56 days, while the older denser cells partitioned in the other chamber initiate their aging loss almost immediately after reinfusion into the circulation so that only half of those cells are alive after 40 days. It is apparent, therefore, that a patient transfused with the younger human red blood cells will require fewer transfusions and, therefore, will accumulate less iron in the circulatory system over a given period of time.

After the fractionated blood has been separated and partitioned as aforesaid, the two chambers are isolated by appropriately sealing and severing the conduit connecting the two chambers. Thus, the container system is separated into two independent sterile chambers, one of which contains blood gerocytes and the other of which contains blood neocytes of a selected mean age along with the blood plasma. The contents of the former chamber can be used for experimentation, blood tests, transfusion for acute blood loss, etc.; the contents of the latter chamber can be used as donor blood for patients suffering from chronic anemia or for others who require the younger blood cells.

Preferably the above method is carried out in a container system whose other chamber is collapsible and filled initially with a sterile saline wash solution. During the high-speed centrifuging step, this chamber collapses and forces the saline solution through the conduit into the one chamber containing the whole blood. The wash solution helps to separate agglomerated blood cells and also avoids the need to add that solution later by violating that chamber. When the method is carried out in the presence of a wash solution, it is desirable that a static seal be provided in the conduit between the two chambers to prevent the wash solution from prematurely entering the chamber to be filled initially with whole blood.

Preferred embodiments of our apparatus will be described in detail presently. Suffice it to say at this point that my method and apparatus permit red blood cells to be separated and to be partitioned at substantially any point along a density or age continuum on a high volume basis while remaining in a sterile environment. Yet the apparatus is relatively easy and inexpensive to manufacture and it is also easy to use by relatively unskilled personnel.

BRIEF DESCRIPTION OF THE DRAWINGS

For a fuller understanding of the nature and objects of the invention, reference should be had to the following detailed description, taken in connection with the accompanying drawings, in which.

DESCRIPTION OF THE PREFERRED EMBODIMENTS

Figure 1:
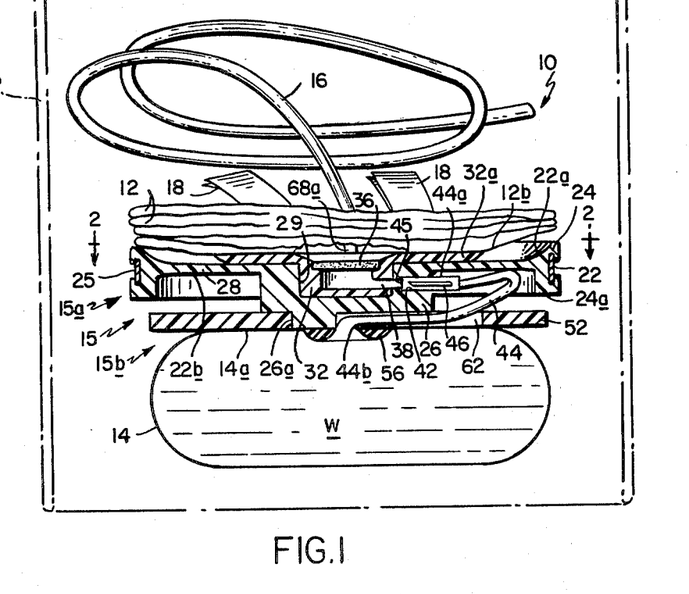
FIG. 1 is an elevational view with parts in section showing apparatus for preparing neocyte enriched blood in accordance with my method, the apparatus being folded and packaged as a kit.
Figure 2:
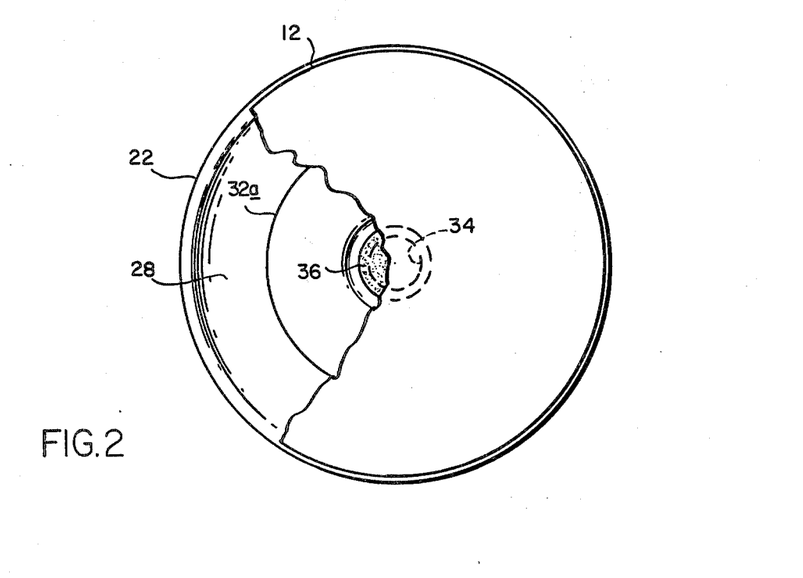
FIG. 2 is a sectional view with parts broken away taken along line 2—2 of FIG. 1.
Figure 3:
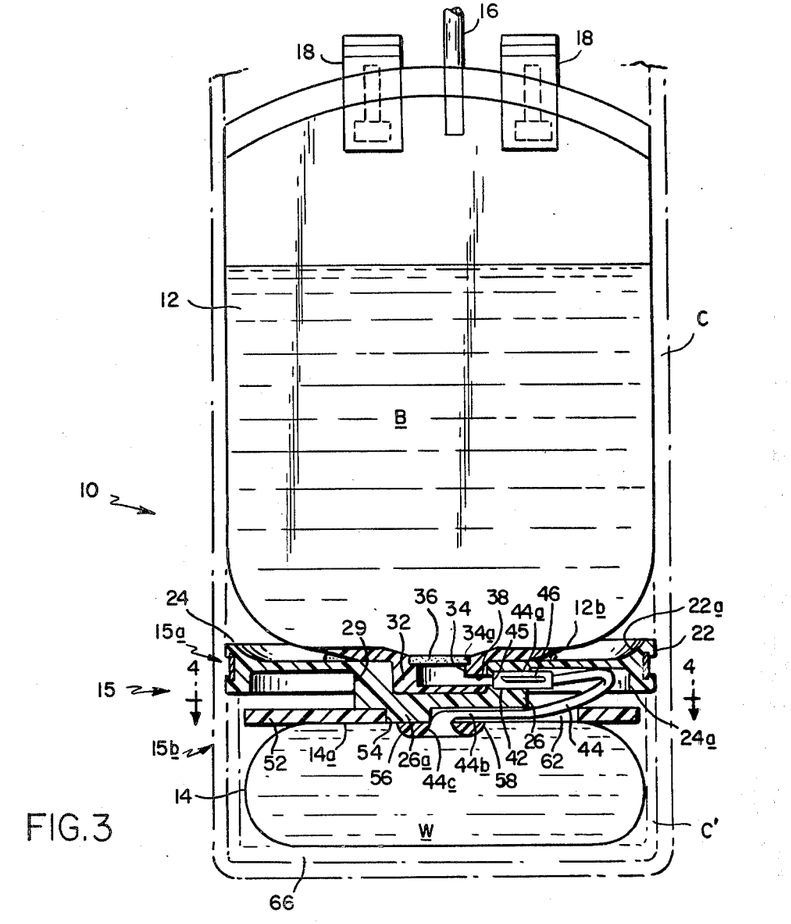
FIG. 3 is an elevational view with parts in section illustrating the FIG. 1 apparatus readied for use.

Referring to FIGS. 1 to 3 of the drawings, the apparatus is indicated generally at 10. Until it is going to be used, apparatus 10 is folded and maintained in a sterile and septic condition within a sealed plastic pouch indicated in dotted lines at P in FIG. 1. Apparatus 10 is basically a container system comprising a relatively large chamber-defining first container 12 and a smaller chamber-defining second container 14. While various types of containers can be used to define the two chambers, in the illustrated embodiment of the apparatus, the two containers are flexible bags or pouches made of any suitable plastic material compatible with the human system and able to withstand autoclaving temperatures, e.g. a PVC copolymer. The bag 12 is similar in its shape and size to a standard blood bag such as depicted in U.S. Pat. No. 3,064,647 used for blood transfusion and blood component separation. In this, the bag is fitted with an inlet tube 16 and removably sealed access ports 18 incorporated into the seam 12a at the upper end of bag 12. The lower end wall 12b of the bag 12 is sealed to the top of a coupling 15.

The bag 12, when empty, is more or less flat and can be folded as depicted in FIG. 1. However, when the bag is filled with liquid and distended, as shown in FIG. 3, at least its lower segment assumes the general shape of a cylinder. FIG. 2 illustrates the bag with that circular cross section.

The flexible bag 14 on the other hand has the general shape of a flattened sphere and the upper surface 14a of that bag may be sealed to the underside of coupling 15.

Referring to FIGS. 1 to 3, the coupling 15 comprises an upper section 15a and a lower section 15b which are removably connected together. Section 15a comprises a disk 22 molded or otherwise formed of an appropriate elastomer able to withstand autoclaving temperatures, e.g. natural rubber. The disk has a relatively thick or high rim 24 within which is contained a metal hoop 25 which makes the rim quite stiff or rigid in the vertical direction. A cylindrical depending boss 26 is formed at the center of the disk. That boss is also relatively thick or high so that it also is stiff and rigid. However, the upper disk surface 22a is dished. Furthermore, the disk underside is dished or recessed in an annular region between the rim 24 and boss 26. Such profiling of the disk leaves a relatively thin annular web 28 extending between the rim and the boss which is quite flexible and resilient in the vertical direction.

A centrally located cylindrical recess 29 extends from the disk upper surface 22a down into boss 26. A cylindrical plug 32 is received in recess 29 which plug has a circumferential flange 32a which engages the disk upper surface 22a. The lower end wall 12b of bag 12 is sealed to the upper surface of that flange.

The plug 32 is formed with a vertical bore 34 which extends from its upper surface part way through the plug and which registers with an opening (not shown) in bag wall 12b. Furthermore the mouth of that bore is counterboarded at 34a for seating a thin discoid filter 36. Registering lateral passages 38 and 42 are formed in plug 32 and boss 26 respectively. An enlarged end segment 44a of a length of tubing 44 is sealed into passage 42 to establish fluid communication with the interior of bag 12. The inner end of that segment is normally closed by a penetrable seal 45. That seal may be punctured, however, by a rigid pointed cannula 46 situated in tube segment 44a. The tubing 44 is contained in the space between coupling sections 15a and 15b. Although only one loop of the tubing is shown in the drawing figures, a longer length of tubing can be wrapped around boss 26 in the space between the two coupling sections. In any event, the lower end 44b of the tubing passes through coupling section 15b and is connected to bag 14 as will be described presently.

Figure 4:
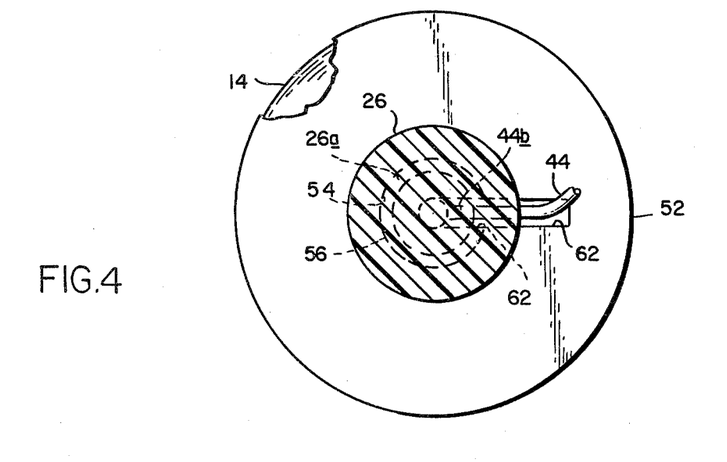
FIG. 4 is a sectional view taken along line 4—4 of FIG. 3.
Figure 6:
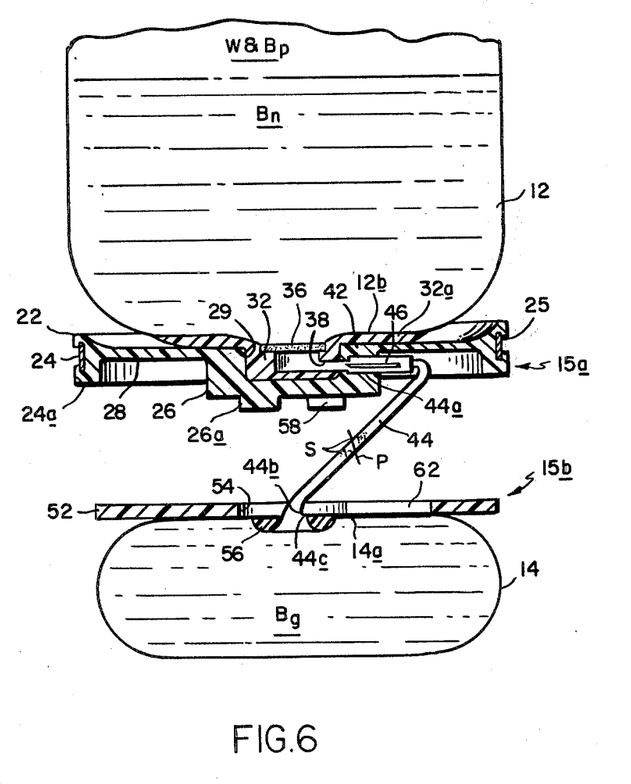
FIG. 6 is a fragmentary elevational view with parts in section showing the apparatus in greater detail and further illustrating its operation.

Referring now to FIGS. 3, 4 and 6, coupling section 15b comprises a rigid plastic disk 52. The upper surface of bag 14 is sealed to the underside of disk 52. Also, the tube end 44b is inserted through a central opening 54 formed in disk 52 and through the top wall 14a of bag 14. The lower edge or lip 44c of the tube is sealed to an annular valve member 56 mounted to the inside surface of bag wall 14a. This the tube 44 provides a direct fluid-tight conduit between bags 12 and 14.

The disk opening 54 is sized to snugly receive a necked-down portion 26a of boss 26 so that the disk can be removably engaged on the boss as shown in FIG. 3. The boss portion 26a and the disk 52 are also provided with registering slots 58 and 62 to accommodate the tube 44 when the disk 52 is engaged on boss 26 as illustrated in that figure.

Referring now to FIGS. 1 and 2, as noted at the outset, the apparatus 10 is normally maintained in a sterile condition within the sealed plastic pouch P. In this condition, the upper bag 12 is folded down as shown and contains an anti-coagulant such as used in the collection of whole blood. The lower bag 14 on the other hand is filled with a saline wash solution W. As stated above, there is a static seal 45 located at the entrance to tube 44 which normally isolates the interiors of bags 12 and 14. This seal prevents the wash solution W in bag 14 from flowing into bag 12 when the apparatus 10 is stored on the shelf. The seal 45 also prevents whole blood contained in bag 12 from flowing prematurely into bag 14 when the apparatus 10 is being readied for use in a manner to be described presently.

In use, the apparatus is removed from pouch P and the bag 12 extended as shown in FIG. 3 and hung from a suitable support while donor whole blood B is introduced into the bag 12 through its inlet tube 16. The volume of blood B introduced into the bag plus anticoagulant already present should not exceed the effective volume of the bag less the volume of the wash solution W in bag 14. As noted previously, the blood remains in bag 12 and cannot flow into bag 14 because of the static seal 45. When ready, the operator breaks seal 45 by pushing cannula 46 through the seal, the tube segment 44a being sufficiently flexible to permit this. The apparatus 10 is then placed in a cylindrical centrifuge container indicated in dotted lines at C in FIG. 3. Snugly seated at the bottom of container C is a rigid removable cup C'. When the apparatus 10 is properly seated in the container C, the flat undersurface 24a of the coupling ring 24 seats on the edge of container C'. Thus container C' establishes the effective volume of the lower chamber 14. In other words while the inside diameter of that cup may be fixed, the cup height may be varied in order to vary the effective volume of bag 14 for reasons that will become apparent later.

Figure 5:
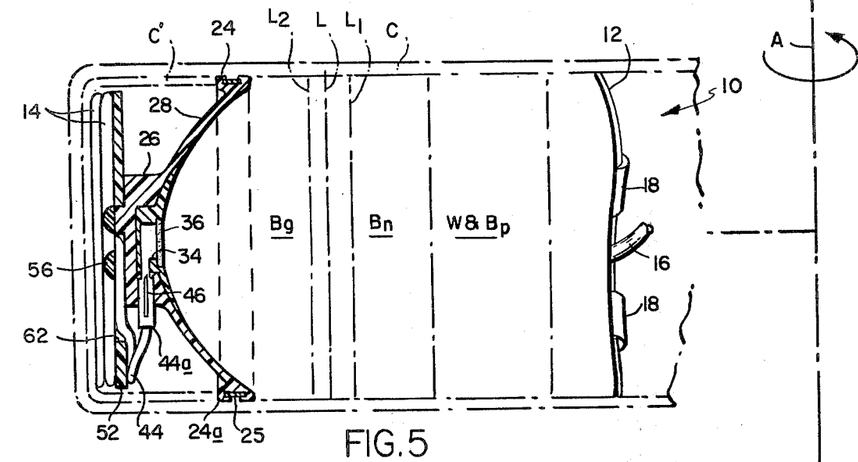
FIG. 5 is a sectional view illustrating the operation of the FIG. 1 apparatus.

As in most centrifuges, the centrifuge container C is mounted on a pivot and is initially oriented vertically. Then when the centrifuge is in operation, the container C is spun at high speed about an axis A illustrated in FIG. 5 giving rise to a centrifugal force in excess of 500 G, whereupon the container swings out sideways as shown in that figure. When container C and its contents are spun thusly, the centrifugal force tends to thrust the bag 12 contents B away from the spin axis A. Since the position of coupling rim 24 is fixed by cup C', the web portion 28 of the coupling section 15a flexes, thereby shifting boss 26 and disk 52 away from the spin axis toward the closed end of container C as shown in FIG. 5. The disk 52 thus squeezes bag 14 so that the solution W in bag 14 is pumped through the nowopen tube 44 into bag 12 where it mixes with the whole blood B therein.

After all of the wash solution in bag 14 has been squeezed out of the bag and the bag has collapsed completely as illustrated in FIG. 5, the valve member 56 seats against the wall of bag 14, forming a dynamic seal at the lower end of tube 44. This seal isolates the interiors of bags 12 and 14 preventing any blood (or wash solution) in bag 12 from flowing into bag 14 during this high-speed centrifuging step.

As the spin cycle continues, the whole blood B in bag 12 and the wash solution introduced into that bag from bag 14 separate in accordance with their densities. That is, the least dense components consisting of the wash solution W and the blood plasma tend to accumulate in a bag zone closest to the spin axis A near the top of bag 12, while the densist blood fractions such as red cells tend to accumulate furthest away from the spin axis at the bottom of bag 12. The intermediate density fractions accumulate in bag zones intermediate those two extremes. Thus the blood fractions separate and form a density continuum in bag 12. While not absolutely necessary, the wash solution is introduced into bag 12 during centrifuging because it helps to break up agglomerated blood cells and thus enhances the formation of the cell density continuum. The solution could also have nutrients added to prolong the shelf life of the red blood cells separated in accordance with this technique.

Figure 7:
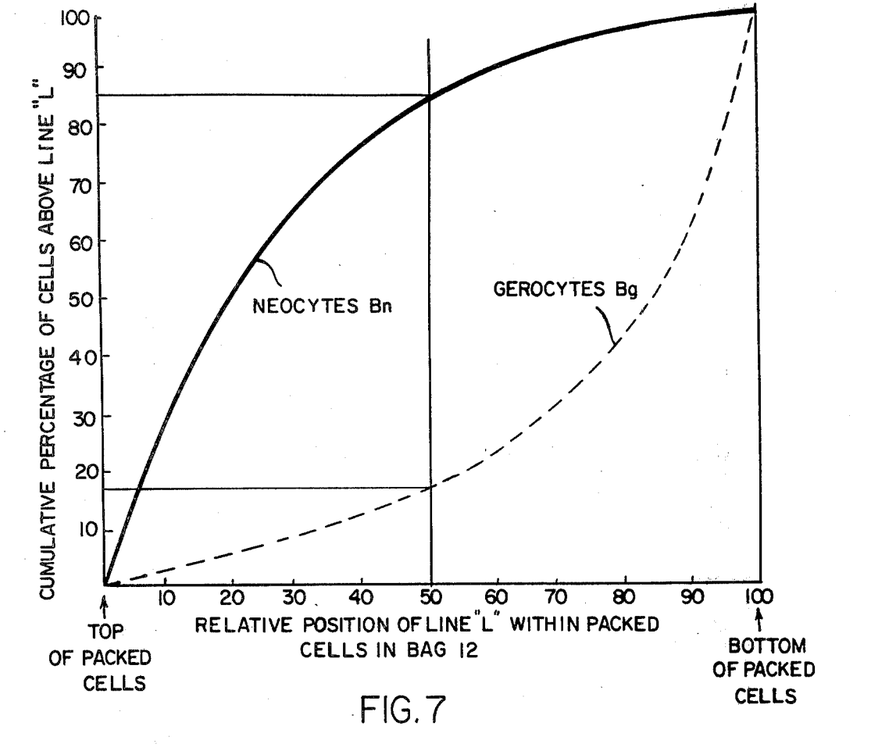
FIG. 7 is a graphical diagram showing the distribution of red blood cells in the FIG. 5 apparatus.

As noted above, there is a direct relationship between the density of the red blood cells and their age. When processed in accordance with this method, then, the separate red blood cells also form an age continuum in bag 12. That is, the older blood cells or gerocytes $B_g$ accumulate at the bottom of bag 12 as illustrated in FIG. 5, while the younger blood cells or neocytes $B_n$ are situated in zones closer to the spin axis A. The lightest blood fractions such as the blood plasma $B_p$ and the wash solution W are located in zones closest to the spin axis, all as shown in FIG. 5. A typical age distribution of the red blood cells in bag 12 is illustrated graphically in FIG. 7.

The high-speed centrifugation cycle continues until the whold blood B has separated and formed the density continuum just described. The length of time that it takes for this to occur depends upon the spin speed. Actually, the product of the centrifuge speed and the spin time is more or less a constant. I have found that adequate density separation or distribution takes place when the centrifuge is operated at a speed of about 2,000 G for approximately 15 minutes.

After that period of time, the centrifuge is slowed to reduce the centrifugal force to below 500 G and preferably to about 200 G. At this low speed, the diaphragm 28 tends to resume its normal unflexed position illustrated in FIG. 3, thereby unseating the valve member 56 and opening tube 44. However, the restoration of the diaphragm is such that there is minimal disturbance of the density continuum established in bag 12. The blood fractions, i.e. the blood gerocytes $B_g$ closest to the bottom of bag 12 are now free to flow through tube 44 into bag 14 under the influence of the relatively small centrifugal force developed at that low spin speed. The filter 36 at the mouth of tube 44 has a pore size on the order of 200 microns so that it readily passes the red blood cells which are only on the order of 7 microns in diameter. However, the filter tends to smooth the flow of the blood cells into bag 14. Also, of course, the filter screens out particulate matter entrained in the fluid leaving bag 12 that might tend to obstruct tube 44.

Progressively less dense blood fractions flow into bag 14 from the bottom of bag 12 as the centrifuge continues to slow down at a relatively low rate. The flow is smooth and the flow rate is such that there is minimum disturbance of the distributed blood components in bag 12. The flow into bag 14 ceases, of course, when the bag becomes completely filled. The effective volume of that bag, therefore, establishes the cut-off or partition line L (FIG. 5) between the more dense older red blood cells which enter bag 14 and the less dense younger blood cells remaining in bag 12 after completion of the process. The fluid flow path into bag 14 is designed so that the transfer of cells into bag 14 is completed before the centrifuge is stopped.

Thus, by varying the effective volume of bag 14, one can shift the partition line L which demarcates the older blood cells $B_g$ which flow into bag 14 and the younger cells $B_n$ which remain in bag 12 after the partitioning step. By this means, then, one can actually control the average density and therefore the average age of the red blood cells remaining in bag 12. In other words, if the volume of bag 14 is increased, more fluid from bag 12 is transferred to bag 14 after the centrifuging step. Effectively, then, the partition line L shown in FIG. 5 which demarcates the blood fractions which are transferred to bag 14 from the ones remaining in bag 12 is essentially moved upwards along the bag, say, to the line shown as the dotted line $L_1$ in FIG. 5. Therefore, as that bag volume is increased, the average density and age of the red blood cells remaining in bag 12 are less Conversely, as the effective volume of bag 14 is decreased, effectively the partition line L is moved downwards toward the lower end of bag 12, say, to dotted line $L_2$ with the result that, after partitioning, the red blood cells remaining in bag 12 have a greater average density and age.

Thus by appropriately selecting the volume of bag 4, one can locate the partition line L so that, say, half of the red blood cells contained initially in bag 12 enter bag 14. In this case, as seen from FIG. 7, approximately 84% of the neocytes remain in bag 12 having an average life expectancy of 90 days, whereas only 16% of the gerocytes remain with an average life-span of 30 days. Hence the average life-span of cells remaining in bag 12 is 80 days ($0.84 \times 90 + 0.16 \times 30$). This is compared with the average life-span of unfractionated red blood cells which is about 60 days. On the other hand, if the effective volume of bag 14 is selected so that the bottom three-fourths of the red blood cells enter bag 14, approximately 60% of the neocytes remain in bag 12 with only about 8% of the gerocytes being present. Since these neocytes include the very youngest cells, their average lifetime is about 98 days. Hence, this more enriched, though smaller quantity of, blood has an average life of about 90 days ($0.60 \times 98 + 0.08 \times 30$ divided by 0.68).

If it is desired to reduce the effective volume of bag 14, one can place the apparatus 10 in container C fitted with a shorter volume-defining cup C'. Initially the coupling rim 24 may not seat on the edge of cup C'. However, as soon as the high-speed centrifuge step starts, the rim is thrust against that edge as the bag 14 collapses and the wash solution W is pumped into bag 12 as described above. At the end of the high-speed centrifuge cycle when the diaphragm 28 resumes its normal unstressed condition illustrated in FIG. 3, the amount of fluid that enters the bag 14 will be determined by the effective internal volume of the cup C' which will be less than the actual volume of the bag. In other words, due to the shorter height of the cup C', the bag 14 will remain partially collapsed so that the amount of fluid that can enter the bag will be less than the actual bag volume. By varying the cup height, then, the average age of the blood cells entering bag 14 and thus the average age of the cells remaining in bag 12 can be adjusted to suit the particular requirements at the time.

It is critical to note that, in accordance with my technique, the whole blood is separated in accordance with a density or age continuum during high-speed centrifugation. However, the thus separated blood fractions are partitioned along the partition line L only after the completion of the high-speed centrifugation step. In other words, the partitioning takes place in the presence of low G forces under 500 G which are just enough to facilitate transfer of the blood fractions into bag 14 without disturbing the density continuum established in bag 12. That is, the low spin speed during partitioning is selected so that there is adequate back pressure when the valve member 56 unseats to open tube 44 so that the fluid flow into bag 14 is not so rapid that it destroys the density gradient established in bag 12. On the other hand, the period of the low speed spin step is selected to provide adequate time for the blood cells to fill the effective volume of bag 14 before the spinning stops entirely.

The blood gerocytes and blood neocytes differ from one another in density by only 1.06 to 1.09 g/ml. Yet using this separation or distribution technique and apparatus, these cells can be separated in bag 12 and partitioned into the two bags 12 and 14 at a demarcation line L which can be selected to be at essentially any point along that density range.

Referring now to FIG. 6, after the blood fractions have been separated and partitioned as aforesaid, the apparatus 10 is removed from the centrifuge container C and the disk 52 is disengaged from boss 26, thereby separating the two coupling sections 15a and 15b as shown in that figure. Then seals S are formed in tube 44 at spaced-apart locations therealong in order to isolate the interiors of bags 12 and 14. Finally, the tube is severed at a point P between the two seals S thereby separating the two bags and their contents. The less dense younger blood cells or neocytes $B_n$ in bag 12 can now be used to infuse patients such as those with chronic anemias having a need for such younder blood cells to avoid iron overdose. On the other hand, the more dense, older blood cells contained in bag 14 can be used for experimentation, testing or to infuse patients having an immediate need of blood of any age, accident victims for example.

If desired, various other valve means may be utilized to isolate the interiors of bags 12 and 14 during the blood fraction separation step which occurs during high-speed centrifugation, and to establish communication between those two chambers during the blood fraction partitioning or segregating step which occurs after that step. For example, a normally closed electrically operated valve can be included in the tube 44. At the end of the centrifuge cycle when the container C is spinning at a low speed, that valve can be opened for a period sufficient to allow a volume of fluid to be transferred from the bottom of bag 12 into bag 14 corresponding to the blood fractions below the selected partition line L.

Figure 8:
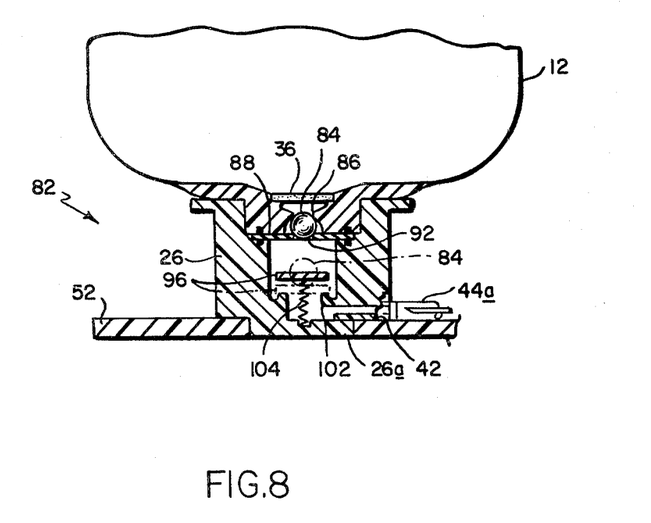
FIG. 8 is a view similar to FIG. 3 showing another embodiment of the apparatus.

Another type of mechanical valve means is illustrated generally at 82 in FIG. 8. In valve means 82, a ball-type valve member 84 is normally maintained seated on a valve seat 86 under filter 36 by a resilient diaphragm 88. The seating of the ball 84 establishes a static seal which normally isolated bags 12 and 14. The diaphragm 88 is formed with a central opening 92 whose diameter is somewhat smaller than that of ball 84 so the ball normally cannot fit through that opening. Positioned below diaphragm 88 is a small disk 96 and directly below the disk is another valve seat 102. A coil spring 104 reacting between the disk and the bottom of boss 26 biases the disk upwards so that it is spaced somewhat from the valve seat. The space below the valve seat 32 communicates with the tube 44 leading to bag 14.

Normally the ball 84 is seated against valve seat 86. However, when apparatus 10 incorporating valve means 82 is spun at high speed, the ball 84 unseats from the seat 86 and is thrust by centrifugal force through the diaphragm opening 92. It, thereupon engages disk 96 and depresses the disk so that the disk seats on valve seat 102 as shown in dotted lines, thereby blocking flow of fluid into tube 44. In other words, during centrifuging at high speed, the valve means 82 is armed, but still remains closed. At the end of the centrifuge cycle when the spin speed is reduced to a relatively low value, e.g. under 500 G, the centrifugal force acting on disk 96 falls below the restoring force of the spring 104 so that the disk unseats from valve seat 102 as shown in solid lines thereby establishing fluid communication between the two bags and permitting the blood fractions at the bottom of bag 12 to flow into and fill bag 14 as described above. Thus the FIG. 8 valve means 82 functions as both a static seal and a dynamic seal which opens and closes automatically at the proper times in the described process.

Of course, other comparable valve structures can be envisioned which will permit the separation and partitioning of blood fractions in accordance with this technique.

Also, while I have described the present apparatus and method in terms of separating and segregating blood neocytes from gerocytes, the same method and apparatus may be used to separate red blood cells or other substances according to their densities. For example, the same technique may be applied to gene growth applications to separate genes over a density continuum and collect only those genes above or below a selected partition line in that continuum.

It will be seen from the foregoing then that, by using the above-described method and apparatus, one can separate, segregate and collect blood cells having different densities and ages very accurately and in a completely sterile environment. The partitioning can be effected at substantially any chosen point in the density or age continuum and that partition point depends upon the method and apparatus themselves and not on any judgment on the part of the operator. Thus, the separation, partitioning and collection of the blood cells can be carried out by relatively unskilled personnel in a relatively short time. Therefore, this technique should find wide application in hospitals and clinics particularly where there is a need for a continuing supply of donor blood composed of the younger blood cells or neocytes.

It will thus be seen that the objects set forth above, among those made apparent from the preceding description, are efficiently attained, and, since certain changes may be made in the above method and in the above constructions without departing from the scope of the invention, it is intended that all matter contained in the above description or shown in the accompanying drawings be interpreted as illustrative and not in a limiting sense.

It is also to be understood that the following claims are intended to cover all of the generic and specific features of the invention herein described.

What is claimed as new and desired to be secured by Letters Patent of the United States is:

1. Apparatus for preparing neocyte-enriched blood comprising
   A. means defining a first chamber,
   B. means defining a second chamber, said chamber-defining means being adapted for mounting in a centrifuge for spinning therewith and having a spinning position,
   C. a conduit connecting the interiors of the two chambers said conduit being positioned at the radially outer portion of said first chamber-defining means in said spinning position,
   D. means for introducing a liquid into the first chamber,
   E. valve means carried by the chamber-defining means and having a seated position blocking said conduit and an unseated position opening said conduit, and
   F. means for seating the valve means when the chamber-defining means are subjected to centrifugal force of predetermined magnitude developed by said spinning for preventing liquid flow from the first to the second chamber as the components of the liquid are distributed in the first chamber along a density continuum and for unseating the valve means when the centrifugal force developed by said spinning drops below said predetermined magnitude to permit the flow of a selected volume of liquid from the first to the second chamber.

2. The apparatus defined in claim 1 wherein said first and second chamber-defining means comprise flexible bags.

3. The apparatus defined in claim 1 and further including a filter in said conduit between said chamber-defining means.

4. The apparatus defined in claim 1 and further including an aqueous wash solution contained in said second chamber-defining means.

5. The apparatus defined in claim 1 wherein said valve means prevent flow of liquid between said chambers until after said chamber-defining means have been spun at high speed.

6. The apparatus defined in claim 5 and further including
   A. a seal preventing flow of liquid through said conduit, and
   B. means for penetrating said seal prior to spinning said chamber-defining means.

7. The apparatus defined in claim 5 wherein said valve means comprise a valve member in said second chamber at the entrance thereinto of said conduit, said valve member being arranged to seat against a wall of the second chamber-defining means when said chamber-defining means are subjected to a centrifugal force of said predetermined magnitude.

8. The apparatus defined in claim 5 wherein the valve means comprise
   A. a first valve seat in said conduit,
   B. a second valve seat in said conduit spaced from said first seat,
   C. a valve member positioned between said valve seats,
   D. means for maintaining said valve member against said first valve seat,
   E. means for unseating said valve member from said first seat and seating said member on said second seat when said chamber-defining means are spun so as to block flow of liquid between said chambers during said spinning, and
   F. means for unseating the valve member from the second seat when the chamber-defining means are subjected to a centrifugal force of less than said predetermined magnitude.

9. Apparatus for separating different density cells comprising
   A. a first flexible bag,
   B. a second flexible bag having a smaller volume than the first bag, said bags adapted for mounting in a centrifuge for spinning therewith and having a spinning position,
   C. a conduit for connecting the interiors of the two bags, said conduit being positioned at the radially outer portion of the first bag in said spinning position,
   D. means for introducing a liquid into the first bag,
   E. means at the conduit end of the first bag for removably mechanically coupling said bags together,
   F. valve means having a seated position blocking said conduit and an unseated position opening said conduit, and
   G. means for seating the valve means when the bags are subjected to centrifugal force of predetermined magnitude developed by said spinning for preventing liquid flow from the first to the second bag as the components of the liquid are distributed in the first bag along a density continuum and for unseating the valve means when the centrifugal force developed by said spinning drops below said predetermined magnitude to permit the flow of a selected volume of liquid from the first to the second bag.

10. The apparatus defined in claim 9 wherein the coupling means includes a male coupling member attached to one of said bags and a female coupling member attached to the other of said bags.

11. The apparatus defined in claim 10 and further including a filter in the conduit between said bags.

12. The apparatus defined in claim 10 wherein one of said coupling members comprises
    A. a relatively rigid outer ring,
    B. a relatively rigid center section attached to one of said bags, and C. a flexible resilient diaphragm connecting said ring and center section so as to permit the center section to shift axially relative to the ring.

13. The apparatus defined in claim 12 wherein the other coupling member comprises a relatively rigid disk attached to the other of said bags.

14. Apparatus for separating different density cells comprising
   A. means defining a chamber adapted for mounting in a centrifuge for spinning therewith and having a spinning position;
   B. a conduit leading from the chamber-defining means for connection to a sealed bag, said conduit being positioned at the radially inner portion of the chamber-defining means in said spinning position;
   C. means at the distal end of the conduit for penetrating the sealed bag;
   D. valve means carried by the bag and having a seated position blocking said conduit and an unseated position opening said conduit, and
   E. means for seating the valve means when the chamber-defining means are subjected to a centrifugal force of predetermined magnitude developed by said spinning and for unseating the valve means when the centrifugal force developed by said spinning drops below said predetermined magnitude to permit the flow of a selected volume of liquid through said conduit to the chamber-defining means.

15. The apparatus defined in claim 14 and further including means for mechanically coupling the chamber-defining means to a bag.

16. The apparatus defined in claim 15
   A. wherein the coupling means includes first and second coupling sections, one section being secured to the chamber defining means adjacent the conduit and the other section being oriented to face a bag.

17. The apparatus defined in claim 16 wherein said one section comprises a first relatively rigid circular member attached to a wall of the chamber-defining means and through which the conduit extends.

18. The apparatus defined in claim 17
   A. wherein said other section comprises a second relatively rigid circular member; and
   B. further including coacting means on said first and second members for removably coupling them coaxially.

* * * * *